United States Patent
Wuske et al.

(10) Patent No.: US 7,374,723 B2
(45) Date of Patent: May 20, 2008

(54) SYSTEM FOR COLLECTING AND RELEASING SALIVA

(75) Inventors: Thomas Wuske, Malente (DE); Torben Bauch, Flensburg (DE); Rainer Polzius, Lübeck (DE); Jessica Mahn, Dunkelsdorf (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 529 days.

(21) Appl. No.: 10/630,958

(22) Filed: Jul. 30, 2003

(65) Prior Publication Data

US 2004/0057876 A1    Mar. 25, 2004

Related U.S. Application Data

(63) Continuation-in-part of application No. 10/417,646, filed on Apr. 17, 2003, now abandoned.

(30) Foreign Application Priority Data

Jul. 31, 2002   (DE) ............................... 102 34 832
Jun. 27, 2003   (DE) ............................... 103 28 984

(51) Int. Cl.
B01L 3/00        (2006.01)
B01L 3/02        (2006.01)
B32B 5/02        (2006.01)
B32B 27/04       (2006.01)
B32B 27/12       (2006.01)
G01N 1/10        (2006.01)
G01N 1/00        (2006.01)

(52) U.S. Cl. .................... 422/100; 422/61; 422/99; 73/864.02; 73/864.91

(58) Field of Classification Search ............. 436/180, 436/174; 422/63, 99–102, 119, 61; 73/863.41
See application file for complete search history.

(56) References Cited

U.S. PATENT DOCUMENTS

| | | | | | |
|---|---|---|---|---|---|
| 3,985,032 | A | * | 10/1976 | Avakian | .................. 73/863.25 |
| 4,635,488 | A | * | 1/1987 | Kremer | .................. 73/864.72 |
| 4,978,504 | A | * | 12/1990 | Nason | ......................... 422/61 |
| 5,567,309 | A | * | 10/1996 | Classon et al. | ............. 210/233 |
| 6,129,894 | A | * | 10/2000 | Rabenecker et al. | .......... 422/61 |
| 6,488,894 | B1 | * | 12/2002 | Miethe et al. | .............. 422/100 |

* cited by examiner

*Primary Examiner*—Jill Warden
*Assistant Examiner*—Keri A Moss
(74) *Attorney, Agent, or Firm*—McGlew and Tuttle, P.C.

(57) ABSTRACT

A device, process and system are provided for collecting and releasing a liquid sample, especially saliva. A defined saliva sample, i.e., a filtered, approximately homogeneously mixed saliva sample of a predetermined volume is made available in the simplest possible manner. A sampling tip (2) is provided made of a dimensionally stable and porous material, which is moved with its mouthpiece (4) in the mouth of a test subject for one to two minutes and takes up saliva based on the capillary action. A reagent liquid enters the pores of the sampling tip (2), mixes with the saliva there and is subsequently fed from a reagent depot by the action of pressure. The saliva and the reagent liquid are finally discharged as a droplet (40) in the filtered and mixed state, either into the cavity (10) of the sample collector or into a filter mixer.

17 Claims, 8 Drawing Sheets

SYSTEM FOR COLLECTING AND RELEASING SALIVA

CROSS-REFERENCES TO RELATED APPLICATIONS

This application is related to German patent application No. 102 34 832.4-35 filed on Jul. 31, 2002 whose priority is claimed under 35 USC §119, the disclosure of which is incorporated herein by reference in its entirety, and to German patent application No. 103 28 984.4 filed on Jun. 27, 2003 whose priority is also claimed under 35 USC § 119, the disclosure of which is incorporated herein by reference in its entirety. This application is a continuation in part of application Ser. No. 10/417,646 filed Apr. 17, 2003 now abandoned, the disclosure of which is incorporated herein by reference in its entirety.

FIELD OF THE INVENTION

The present invention pertains to a device and a process for collecting and releasing a sample liquid, especially saliva.

BACKGROUND OF THE INVENTION

Saliva has gained increasing significance as an information carrier, especially for medical tests as well as for the detection of administered or ingested substances, especially drugs or habit-forming drugs. The testing of saliva is preceded by the taking and providing of a saliva sample.

A device for collecting and releasing saliva for diagnostic purposes has been known from DE 197 48 331 C1. The device comprises a section which collects and squeezes out the saliva sample and is located displaceably in a container. The container is closed at one of its ends and can be opened at its other end by lifting a closing cap with an integrated filter. The container is preferably designed as a bellows. Saliva first enters the bellows via the opened closing cap and is taken up by the porous section. Pushing together the bellows with the closing cap closed presses together the porous section, and the saliva taken up before is discharged to the outside, filtered by the filter of the closed closing cap. The piston is subsequently introduced into a syringe, in which a diluting liquid as well as additional reagents are contained.

SUMMARY OF THE INVENTION

The object of the present invention is to propose a device and a process for collecting and releasing a sample liquid, especially saliva, with which simple sampling and supplying of a defined saliva sample is possible. A defined saliva sample is defined as a filtered, homogeneously mixed saliva sample of a predetermined volume.

The object is accomplished according to the present invention with a device for collecting and releasing a sample liquid including a sample collector with a porous and dimensionally stable sampling tip for taking up the sample liquid in the sampling tip and a means for generating an overpressure or a vacuum in the pores of the sampling tip to release the sample liquid from the sampling tip.

According to another aspect of the invention, a system is provided with the device for collecting and releasing a sample liquid and with a filter mixer with a porous and incompressible filter reactor. The sampling tip and the filter reactor designed complementarily thereto form a positive-locking connection of an approximately constant thickness. The mean pore size of the sampling tip and that of the filter reactor are advantageously between 0.2 $\mu m$ and 200 $\mu m$, and the mean pore size of the sampling tip is advantageously greater than that of the filter reactor.

According to another aspect of the invention, a process is provided for collecting and releasing a sample liquid. The sample liquid is taken up by a, porous and dimensionally stable sampling tip and an overpressure is generated by a means in the pores of the sampling tip. The sample liquid is released through the sampling tip.

The device, system and the process for collecting and releasing a sample liquid are especially suitable for collecting and releasing a saliva sample. Other human body fluids, such as blood, blood plasma, urine or sweat may also be considered as sample liquids. The device comprises a sample collector with a sampling tip made of a porous and dimensionally stable, preferably extensively incompressible material, which is used to collect the sample liquid. The sampling tip is introduced into the oral cavity of a test subject in the case of a saliva sample. The porosity of the sampling tip brings about the uptake of saliva based on capillary forces. Its porosity makes possible the uptake of a precisely predetermined volume. Furthermore, a means is provided, which generates an overpressure in the pores of the sampling tip and thus delivers the sample liquid from the sampling tip, e.g., either to the outside into a filter mixer, or to the inside, into a cavity, i.e., a recess inside the sample collector, which is located opposite the side of the sampling tip.

An overpressure may be generated in the pores of the sampling tip by means of, e.g., a pneumatically or hydraulically operating means. The means is preferably displaceable in relation to the sample collector, the pushing together of the means and the sample collector generating the overpressure in the pores of the sampling tip.

A pneumatically operating means may be operated, e.g., mechanically or by means of a compressed air reserve. It can thus be displaced relative to the sample collector like a reciprocating pump, and it is designed essentially as a pneumatic cylinder, which encloses the sample collector during the pushing together, or as a pneumatic plunger, which penetrates the sample collector during the pushing together.

In case of a mechanically operating pneumatic means, the admission of a reagent liquid from a reagent container may be brought about, besides by an overpressure, during the pressing together of the pneumatic means and the sample collector. A pneumatic unit has, e.g., a reagent depot for this purpose, which is sealed with a foil and is cut up over the edge of the cylinder tube of the sample collector, designed as a puncturing cylinder. A pneumatic plunger has, e.g., a puncturing tip at its lower end, with which the membrane of a reagent capsule located in the sample collector is punctured.

In case of a mechanically operating hydraulic means, sealing to a beaker-like reagent container, into which the sample collector is introduced from the top, can be brought about preferably by means of a sealing lip arranged at the sample collector. Reagent liquid present in the reagent container is then pressed into the pores of the sampling tip. This is achieved by applying pressure on the sample collector, as a result of which an overpressure is generated in the volume that is defined by the sample collector and the beaker-shaped reagent liquid and is enclosed by the sealing lip of the sample collector. When placed on the reagent container, the sealing lip displaces excess reagent liquid into an overflow channel, which extends along the inner side at the top edge of the reagent container. A permanently predetermined volume of reagent liquid is thus left between the sample collector and the reagent container.

In the case of sampling saliva, the sampling tip is part of a mouthpiece, which is made of a material that is medically safe concerning the contact with the mucosa. A combination of different such materials is also conceivable. The peculiarity of the material is in its dimensional stability, which is preserved during the uptake of liquid, especially during sampling in the oral cavity of a test subject. The mouthpiece is pressed against the bracket, so that sealing is achieved between the two parts. The material is, moreover, hydrophilic, e.g., it is pressed cellulose, a cellulose derivative, cotton or a composite thereof. Plastics are also conceivable, such as polypropylene, polyethylene and polyurethane. The use of a material with a porosity gradient, i.e., with a variable pore size depending on the location of the pores in relation to the surface of the mouthpiece, is especially advantageous. Thus, a coarser porosity close to the surface of the mouthpiece at first brings about a strong capillary action, and a finer porosity in a farther inward area of the mouthpiece guarantees a stronger filter action. A porosity gradient thus oriented will serve its purpose in case the sample liquid is delivered in the inward direction into the cavity of the sample collector. Instead of a homogeneous material or material composite, it is possible as an alternative to manufacture the mouthpiece as an incompressible sieve material in the sense of a skeleton with a porous, absorbent and sponge-like content in it. The dimensional stability of the mouthpiece also ensures the precise capture of the volume of sample liquid taken up.

In another preferred embodiment, the sampling tip has an indicator zone outside the mouthpiece which comes into contact with the mouth of a test subject. The indicator zone contains a moisture indicator, which indicates the successful and sufficient collection of sample liquid. If the moisture indicator is an indicator dye, it indicates a change in color in the presence of moisture, and if it is a material that expands in the presence of moisture, e.g., a sponge, the moisture is indicated by a corresponding change in length.

In an advantageous embodiment, the indicator zone is designed as an indicator tab, i.e., as a terminal part of the mouthpiece. It is formed, e.g., from the same material as the mouthpiece, and a food-grade dye, which had been applied and dried before, is located in the front part of the indicator tab facing the mouthpiece. After sample liquid has been taken up by the mouthpiece, it enters a color-marked area, partially dissolves the dye and transports the dye to the end of the indicator tab. A bracket surrounding the mouthpiece is made transparent at least in this section, so that the successful and sufficient sampling can be visually checked from the outside.

Other advantageous embodiments of the present invention comprise a system that comprises the device according to the present invention in a preferred embodiment and, moreover, a filter mixer with a porous and incompressible filter reactor. The sampling tip and the filter reactor may be brought into connection with one another in a positive-locking manner and thus form a unit of an approximately constant thickness, through which the sample liquid as well as the reagent liquid pass to the outside. The mean pore size of the sampling tip and of the filter reactor may be between 0.2 μm and 200 μm each, the mean pore size of the filter reactor may be selected to be smaller, e.g., between 7 μm and 12 μm, than that of the sampling tip, which is, e.g., between 15 μm and 45 μm. Filtering and mixing are facilitated by the pore size for the sample liquid and the reagent liquid decreasing progressively on their path through the sampling tip and the filter reactor. The remarks made above concerning the porosity gradient are analogously applied here.

Furthermore, an advantageous design of a system is possible which comprises in an advantageous embodiment, besides the device according to the present invention, a reagent container of a beaker-like shape for receiving the sampling tip, so that the sampling tip and the inner surface of the reagent container tightly enclose a volume. Overpressure is now generated in the pores of the sampling tip by applying pressure on the sample collector and consequently on the volume enclosed by the sampling tip and the reagent container.

The process according to the present invention for collecting and releasing a sample liquid is advantageously followed by the analysis and evaluation of the sample liquid, which is optionally mixed with a reagent liquid from a reagent container.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1A:
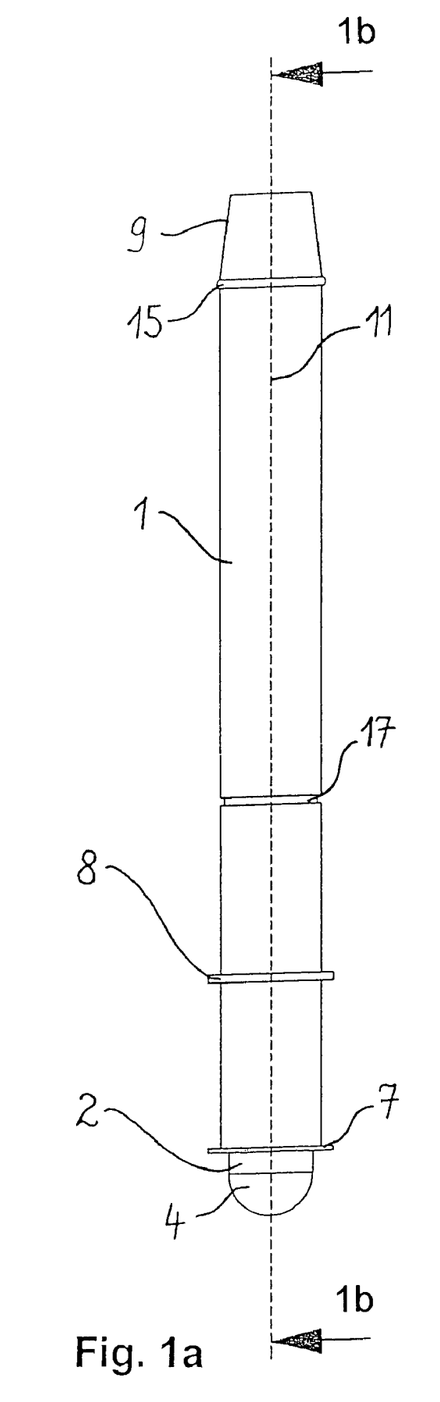
FIG. 1a is a side view of a sample collector.
Figures 5A, 5B:
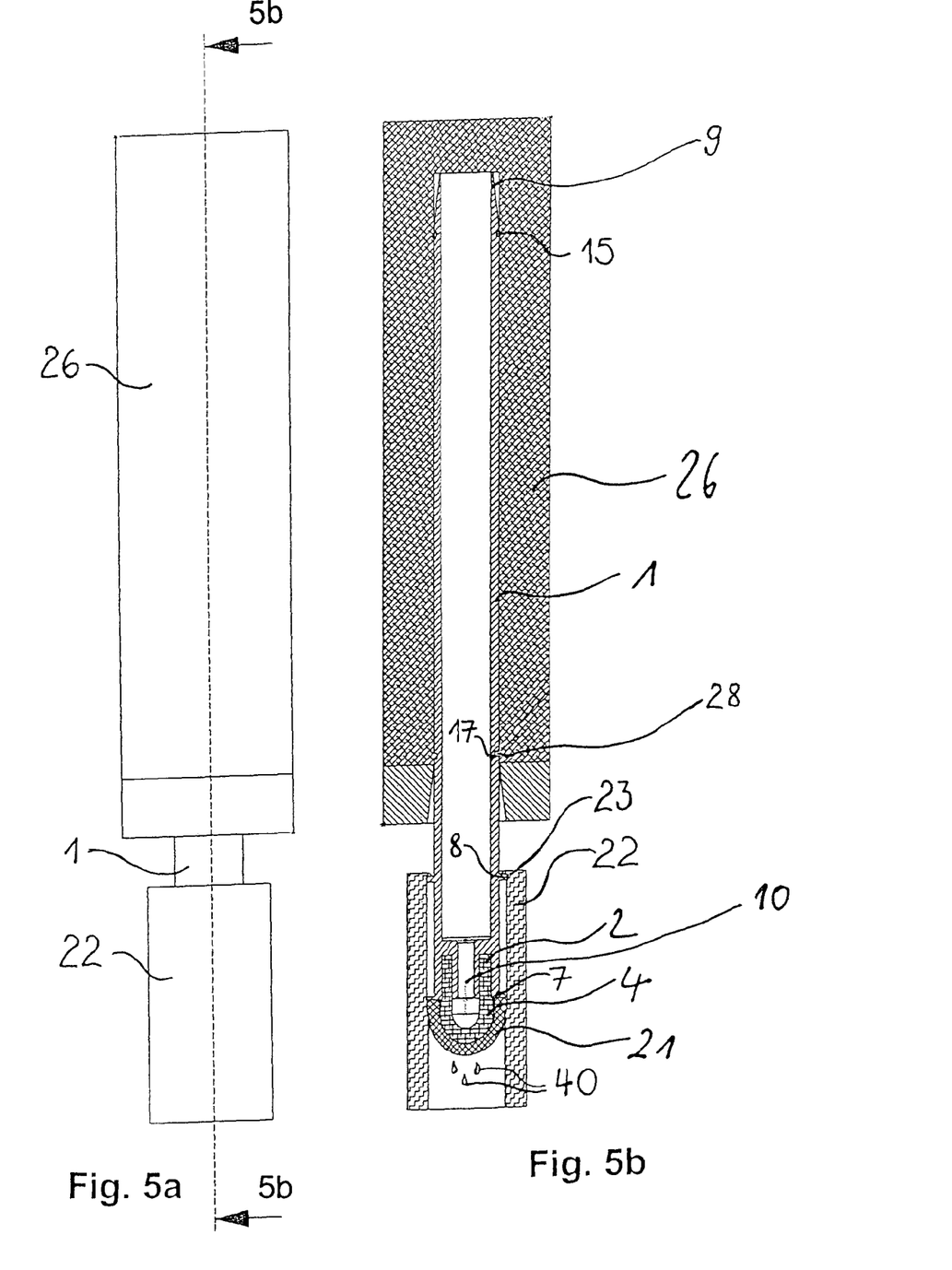
FIG. 5a is a side view of a first alternative of a system with a sample collector, a filter mixer and a pneumatic unit.
FIG. 5b is a longitudinal section of the system according to FIG. 5a along line 5b-5b.

Referring to the drawings in particular, FIG. 1a shows a side view of a preferred embodiment of a sample collector at right angles to its longitudinal axis 11. The sample collector is rotationally symmetrical to the longitudinal axis 11 and comprises a cylinder tube 1, which is joined by a puncturing cylinder 9 at the top end and by a sampling tip 2 at the lower end. The cylinder tube 1 consists of a thermoplast that can be subjected to injection molding, e.g., polypropylene or polyethylene, a machined duroplast or a metal. The sampling tip 2 is closed off with a hemispherical mouthpiece 4, which is introduced into the mouth of a test subject, not shown. A sealing lamella 7 extending around the cylinder tube 1 in a ring-shaped pattern as well as a holding bead 8 extending in a ring-shaped pattern over it guarantee a reliable and accurately positioned sealing against the filter mixer shown in FIG. 2. The sealing formed by the sample collector and the filter mixer can be recognized in FIG. 5b. A groove 17 extending in a ring-shaped pattern around the cylinder tube 1 enables the flange 28 of the pneumatic unit in FIG. 3 to snap in. The pneumatic unit snapped into the groove 17 of the sample collector is shown in FIG. 5b. A recess with an O-ring 15 is provided in the upper area of the cylinder tube 1 below the puncturing cylinder 9 to ensure airtight closure between the sample collector and the pneumatic unit shown in FIG. 3.

Figure 1B:
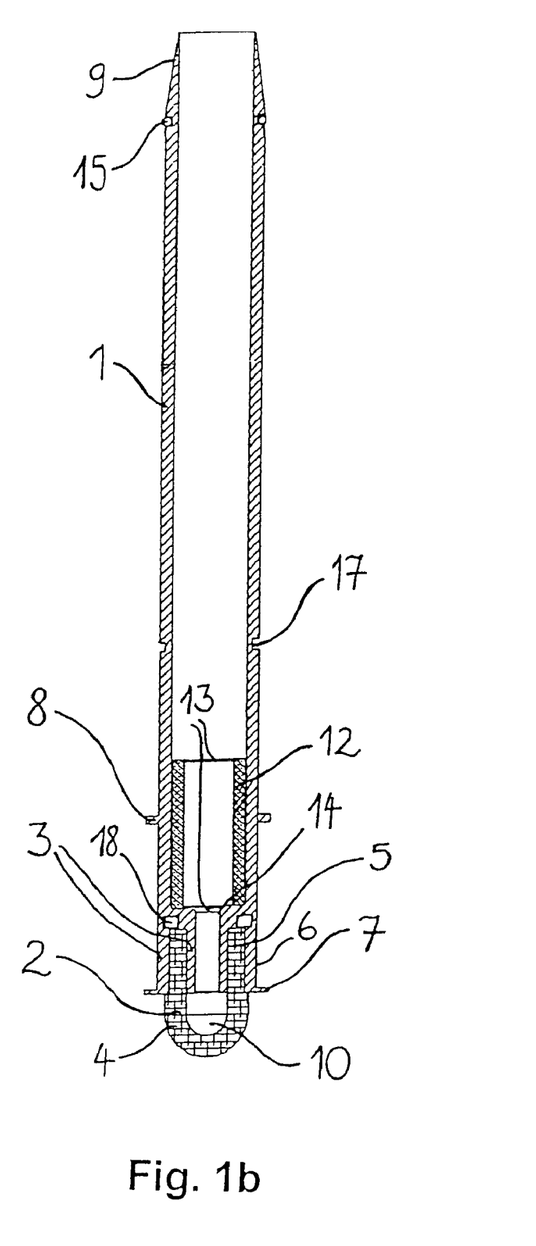
FIG. 1b is a longitudinal section of the sample collector according to FIG. 1a along line 1b-1b.

FIG. 1b shows the longitudinal section of the sample collector according to FIG. 1a along line 1b-1b. The cylinder tube 1 opens downwardly into the upper part of the sampling tip 2 via a bracket 3 of a shaft-like design. The bracket 3 is used, moreover, to separate the mouthpiece 4 and to close off the sampling tip 2 from the indicator zone 5, which forms the part of the sampling tip 2 above the mouthpiece 4. The bracket 3 is transparent in the collection area for the sampling tip 2 in order to make it possible to indicate the moistening through a window. The sampling tip 2 is hollow on the inside and has a constant wall thickness. The cavity 10 in the sampling tip 2 can accommodate a reagent liquid introduced by the pneumatic unit according to FIG. 3. The sampling tip 2 is made of a dimensionally stable and porous carrier material, e.g., sintered ceramic or sintered plastic such as polyethylene, polypropylene, polytetrafluoroethylene, polyvinylidene fluoride or polyurethane. The mean pore size of the carrier material is between 0.2 and 200 µm and preferably between 15 µm and 45 µm, and it is always greater than that of the complementary filter reactor 21 of the filter mixer shown in FIG. 2. The carrier material of the sampling tip 2 has a hydrophilic surface as a consequence of a physical treatment or chemical coating with anionic, cationic or nonionic wetting agents. The physical treatment may be carried out with an ion source. The wetting agents are food-grade wetting agents, e.g., nonionic taurates. In addition, the carrier material may be treated with additives that bring about a concentration, improved solubility or stabilization of an analyte to be detected. The stabilization may be achieved, e.g., by complexing. The indicator zone 5 of the sampling tip 2 does not come into direct contact with the mouth of a test subject. It is prepared by applying a liquid indicator dye to the upper area of the sampling tip 2 and allowing it to dry there. A change in the color of the indicator substance, which can be perceived through the window 6, may indicate, e.g., whether the saliva sample has reached the necessary volume. Suitable indicator dyes include those that indicate a change in the pH value or detect the enzyme amylase present in the saliva. A reagent liquid, which enters the cavity 10 when the puncturing tip 31 of the pneumatic plunger according to FIG. 4 punctures the membrane 13 at the upper and lower ends of the reagent capsule 12, is contained in a reagent capsule 12 optionally arranged in the cylinder tube 1 with a perforable membrane 13 each at the upper and lower ends. The reagent capsule 12 is positioned in the cylinder tube 1 by means of a stop 14.

Figure 2:
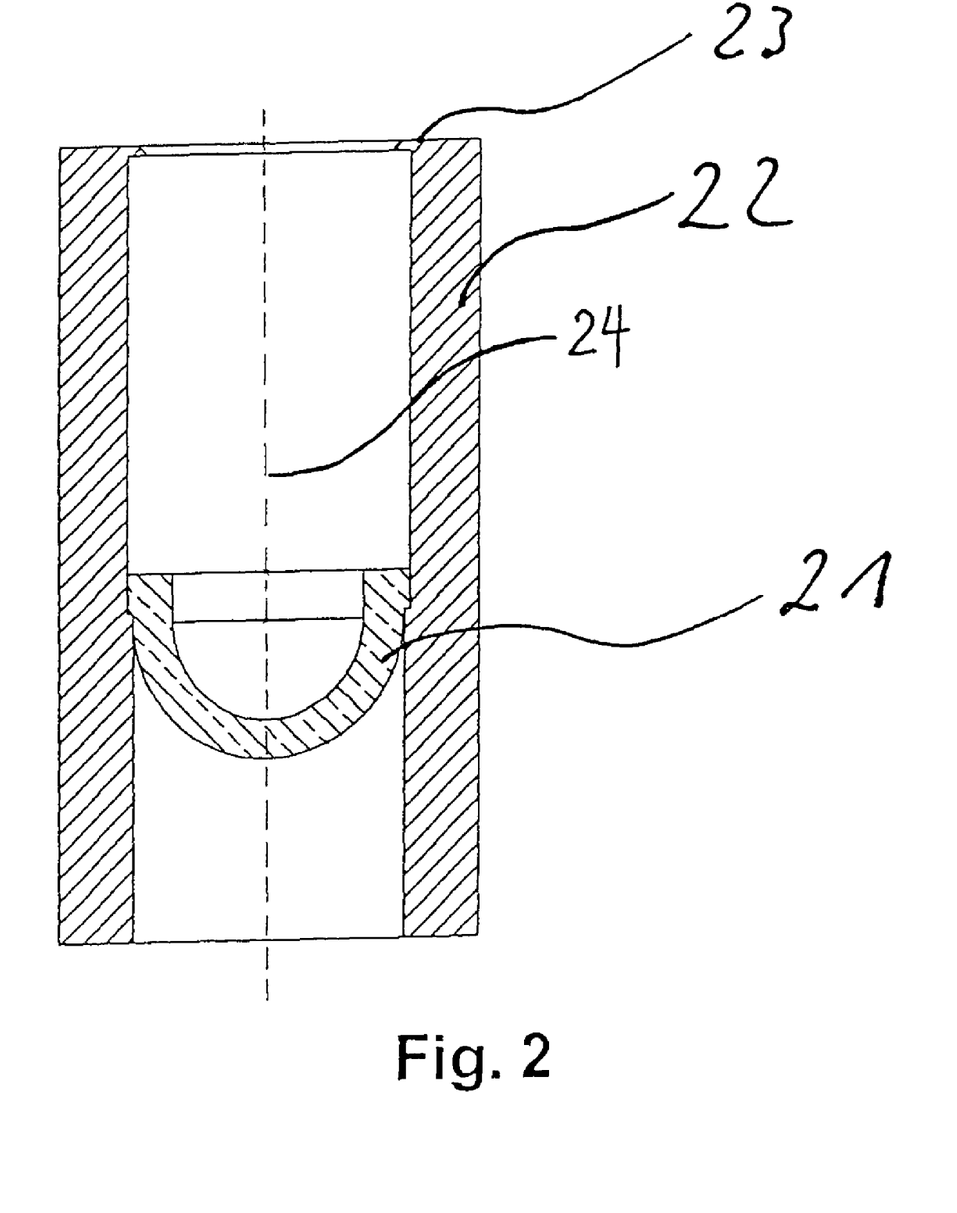
FIG. 2 is a longitudinal section of a filter mixer.
Figure 3:
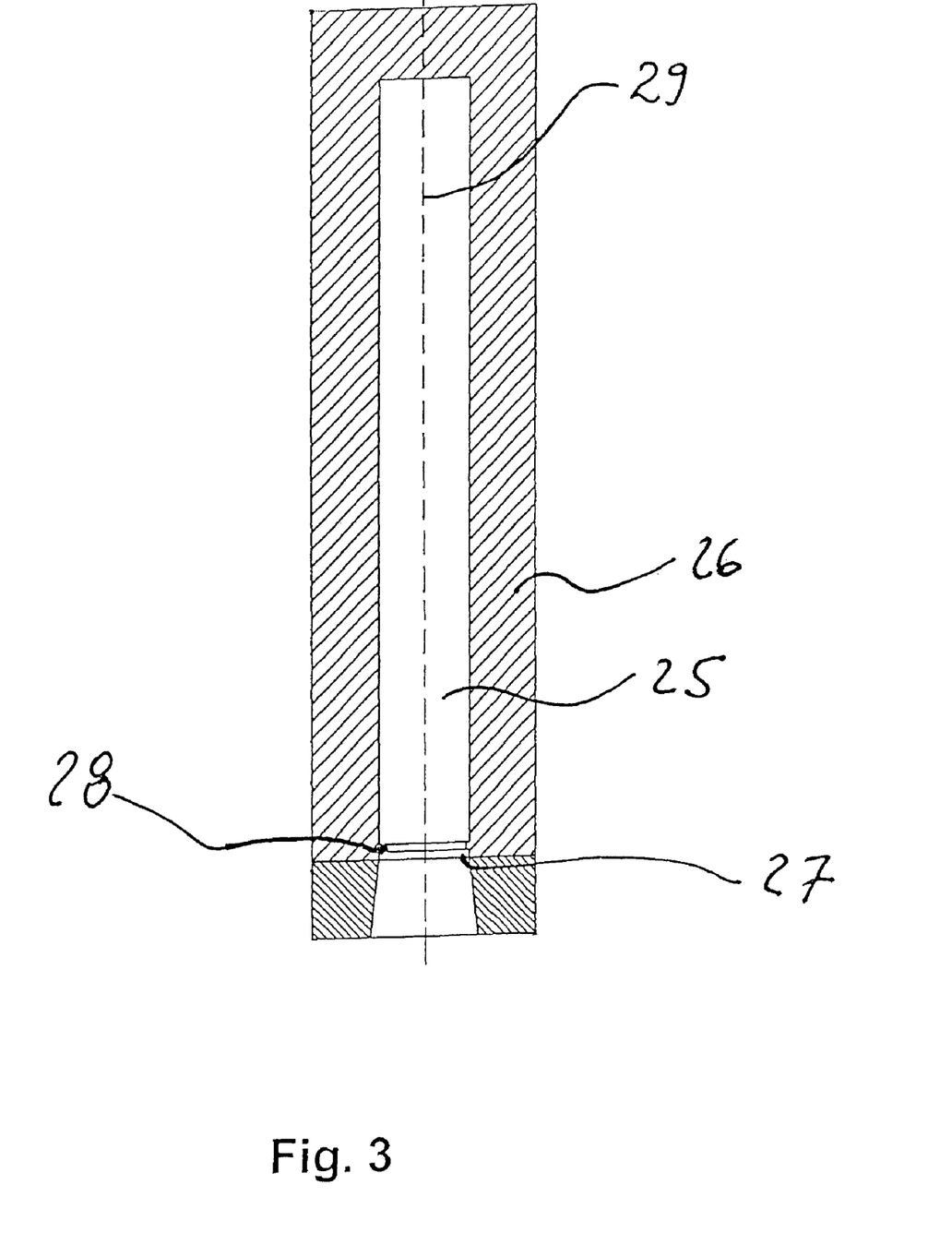
FIG. 3 is a longitudinal section of a pneumatic unit.
Figure 4:
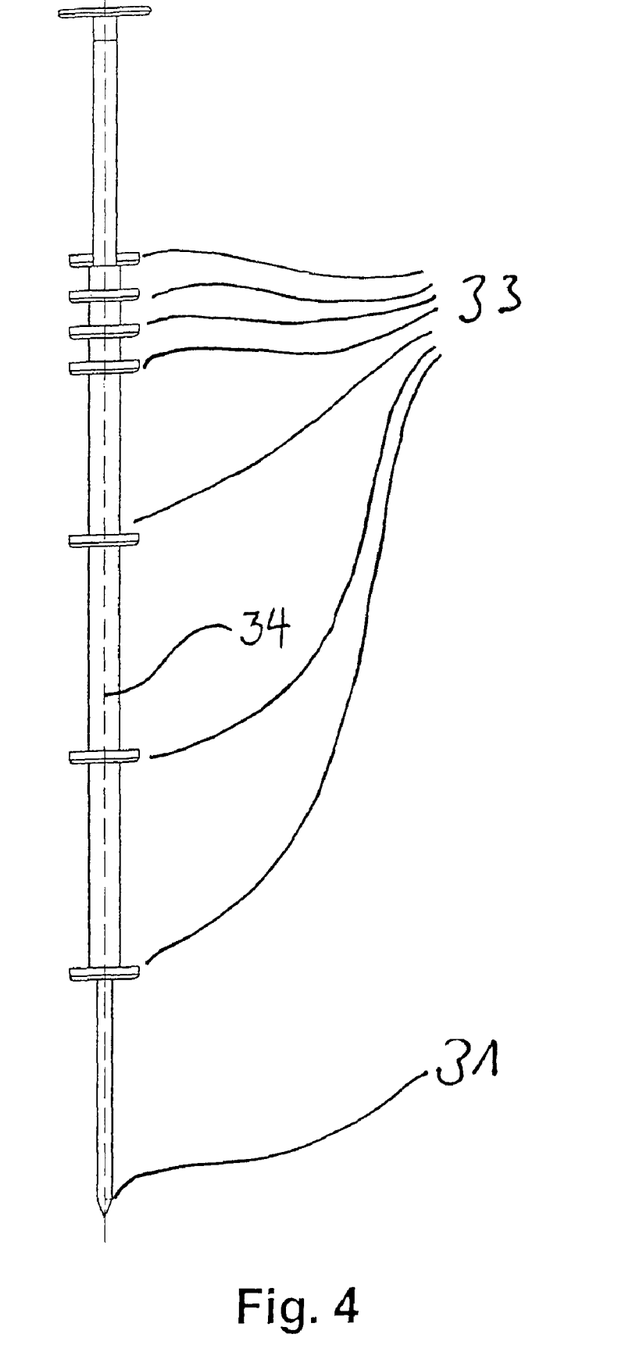
FIG. 4 is a longitudinal view of a pneumatic plunger.

It shall be pointed out here that a pneumatic unit according to FIG. 3 or a pneumatic plunger according to FIG. 4 is used alternatively at the sample collector according to FIG. 1b. If a pneumatic unit according to FIG. 3 is selected, the reagent liquid is introduced via a reagent depot 25. In case of a pneumatic plunger according to FIG. 4, the reagent liquid is discharged from a reagent capsule 12 in the sample collector. It is decisive in both cases, i.e., in case of the use of both a pneumatic unit and a pneumatic plunger, that an overpressure be generated in the cavity 10, which presses the saliva present in the porous wall of the mouthpiece 4 through the wall of the mouthpiece 4 and of the filter reactor 21 of the filter mixer according to FIG. 2 to the outside. The additional release of a reagent liquid is not absolutely necessary. Besides the indication by the indicator zone 5 of whether the saliva sample having penetrated the wall of the mouthpiece 4 has reached the necessary volume, this indication may also be brought about by means of a sponge 18, which is located in the cylinder tube 1 above the sampling tip 2. The sponge 18 consists, e.g., of compressed and colored viscose or cellulose, which expands several times on contact with the saliva. A corresponding change in the length of the sponge 18 on contact with the saliva is visible through the window 6.

FIG. 2 shows a longitudinal section of a filter mixer through its longitudinal axis 24, in relation to which it is rotationally symmetrical. It comprises a guide cylinder 22 and a hemispherical filter reactor 21, which is open upwardly and is inserted at its circular edge into the guide cylinder 22 such that the filter mixer is closed downwardly. The same materials may be used for the guide cylinder 22 as for the cylinder tube 1 of the sample collector according to FIG. 1a. An inwardly protruding, annularly extending holding edge 23 at the upper end of the guide cylinder 22 engages the filter mixer via the holding bead 8 during the fitting together of the sample collector according to FIG. 1a with the filter mixer such that the sample collector and the filter mixer snap into each other. When the filter mixer and the sample collector are fitted together, the filter reactor 21 forms a positive-locking connection with the mouthpiece 4 of the sample collector. The same materials may be used for the filter reactor 21 as well as for the sampling tip 2 of the sample collector according to FIG. 1a. A mean pore size between 0.2 µm and 200 µm is selected in this case as well. It shall be ensured that the mean pore size of the filter reactor 21 is smaller than that of the sampling tip 2. It is preferably between 7 µm and 12 µm. Dry reagents may be considered for use as additives for the material of the filter reactor 21. These are, e.g., antibodies, enzymes, catalysts, mediators, tracer chemicals, stabilizers and buffers.

FIG. 3 shows the longitudinal section of a pneumatic unit through its longitudinal axis 29, in relation to which the pneumatic unit is rotationally symmetrical. It has a pneumatic cylinder 26, which is closed at the top and in which a reagent depot 25 with a reagent liquid is contained, which depot is closed to the outside by a foil 27 sealed in an airtight manner. A ring-shaped flange 28, which snaps into the groove 17 when the pneumatic unit is fitted together with the sample collector shown in FIG. 1b, extends in the lower area of the pneumatic cylinder 26 on the inner side. The inner side of the pneumatic cylinder 26 widens in the lower area toward the edge, so that the tubular wall of the pneumatic cylinder 26 converges in the downward direction. This embodiment makes possible a simpler assembly of the pneumatic unit and the sample collector.

FIG. 4 shows the longitudinal section of a pneumatic plunger through its longitudinal axis 34. The pneumatic plunger is rotationally symmetrical to the longitudinal axis 34. It may be fitted together with the sample collector shown in FIG. 1b and represents an alternative to a pneumatic unit according to FIG. 3. A puncturing tip 31, which perforates the membrane 13 at the upper and lower ends of the reagent capsule 12 during the fitting together of the pneumatic plunger and the sample collector, is located at the lower end. The lamellae 33 arranged in an annular pattern at different heights around the pneumatic plunger are used for sealing against the inner wall of the cylinder tube 1 of the sample collector.

FIG. 5a shows a side view of a first alternative of a system with a sample collector, a filter mixer and a pneumatic unit.

FIG. 5b shows the longitudinal section of the system according to FIG. 5a along line 5b-5b. A saliva sample was already released and has entered the wall of the mouthpiece 4. The sample collector and the filter mixer are plugged together, and the holding edge 23 of the filter mixer engages the holding bead 8 of the sample collector, and the mouthpiece 4 of the sample collector and the filter reactor 21 of the filter mixer form a positive-locking connection. The pneumatic unit was fitted to the sample collector, so that the puncturing cylinder 9 has already punctured the foil 27 of the pneumatic unit, and the reagent liquid has entered the cavity 10 of the sampling tip from the reagent depot 25. The pneumatic unit was fitted farther onto the sample collector until the flange 28 snapped into the groove 17, so that overpressure has meanwhile built up in the cylinder tube 1 and the cavity 10, which presses the saliva, the reagent liquid and optionally additional substances through the mouthpiece 4 and the filter reactor 21 in the downward direction in a filtered, mixed and correspondingly conditioned manner, which is indicated by the droplets 40 dropping off.

Figure 6:
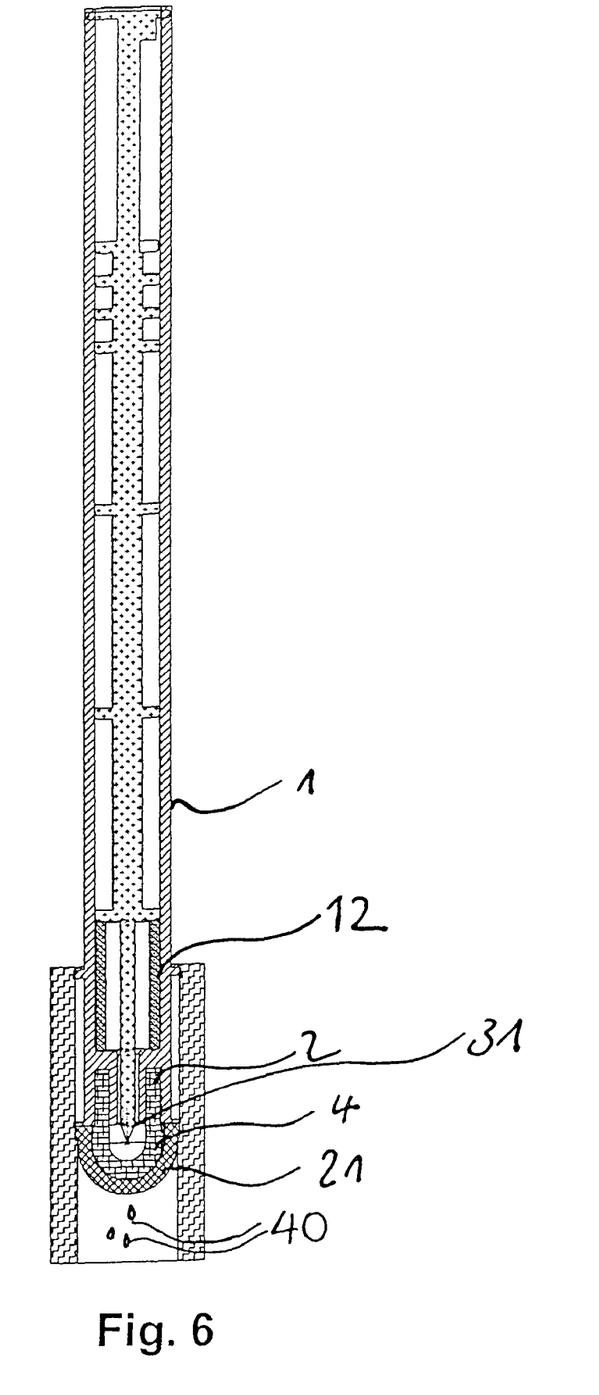
FIG. 6 is a longitudinal section of a second alternative of a system with a sample collector, a filter mixer and a pneumatic plunger.

FIG. 6 shows a longitudinal section of a second alternative of a system with a sample collector, a filter mixer and a pneumatic plunger. The saliva sample was already released in this case as well. The sample collector and the filter mixer have formed a plug-in connection, which corresponds to that in FIG. 5b. The pneumatic plunger was introduced into the sample collector, and the puncturing tip 31 has punctured the membrane 13, not shown here, at the upper and lower ends of the reagent capsule 12, so that the reagent liquid has already entered the cavity 10. The pneumatic plunger was introduced into the sample collector to the extent that the overpressure generated thereby presses the saliva, the reagent liquid and optionally additional substances through the mouthpiece 4 and the filter reactor 21 in the downward direction in a filtered, mixed and correspondingly conditioned manner, which is indicated by the droplets 40 dropping off in this case as well.

Figure 7A:
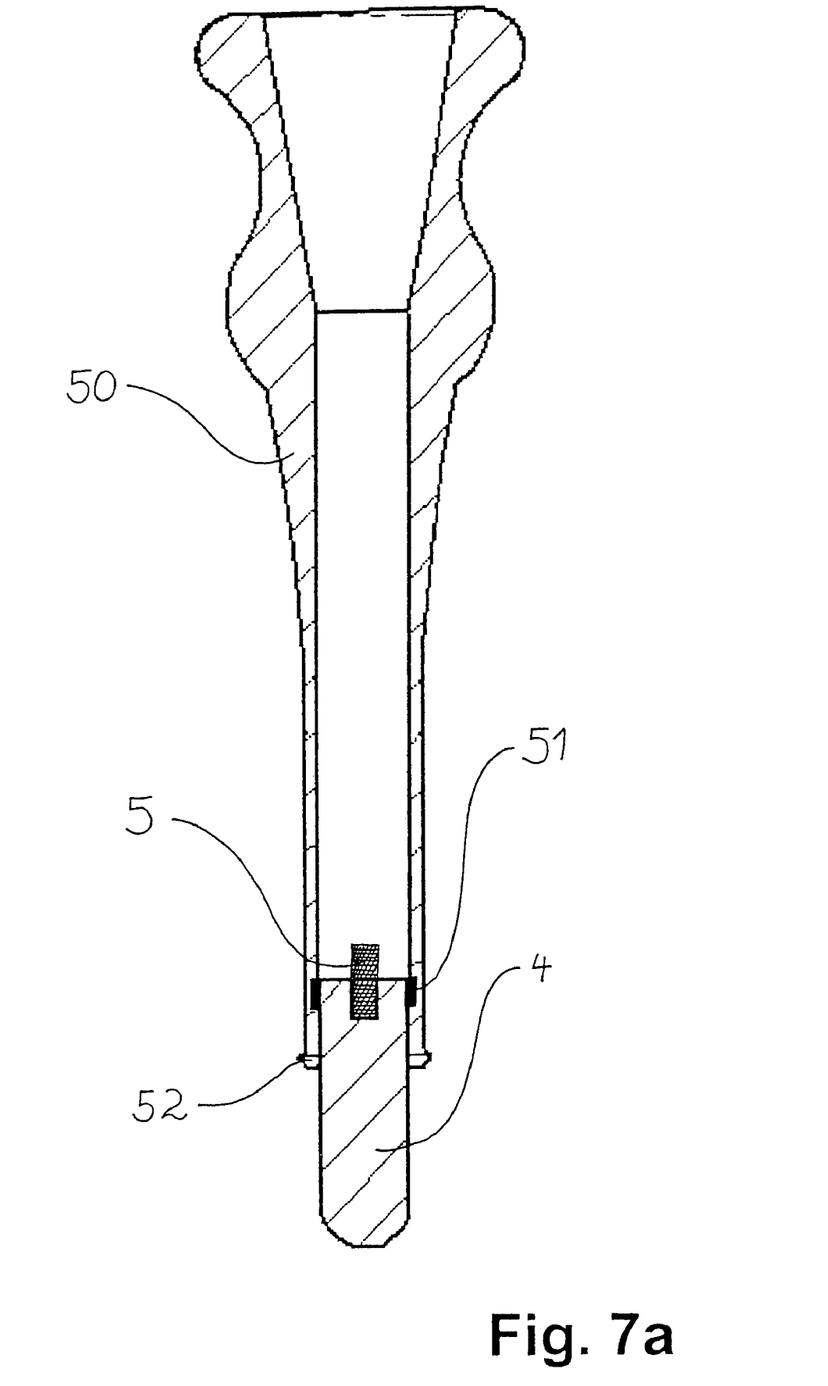
FIG. 7a is a longitudinal section of another sample collector.

FIG. 7a shows a longitudinal section of another sample collector. The indicator zone 5 is designed as an indicator tab here. The sample collector is accommodated by a sleeve 50 shaped ergonomically as a grip. The design allows for a simple introduction of the sample collector into the oral cavity of a test subject. The mouthpiece 4 is sealed by the sleeve 50 toward the outside and is positioned displaceably at the front end of the sleeve 50, with about two thirds of its overall length protruding from the sleeve 50. To prevent the mouthpiece 4 with the indicator tab 5 from falling out, a projection 51 designed as a holding edge is located at the rear end of the mouthpiece 4. A sealing lip 52 closes off a volume formed between the sample collector and the reagent container 47 shown in FIG. 7b, so that an overpressure can be generated in the pores of the sampling tip 2 by applying pressure on the sleeve 50 and the sample collector connected thereto.

Figure 7B:
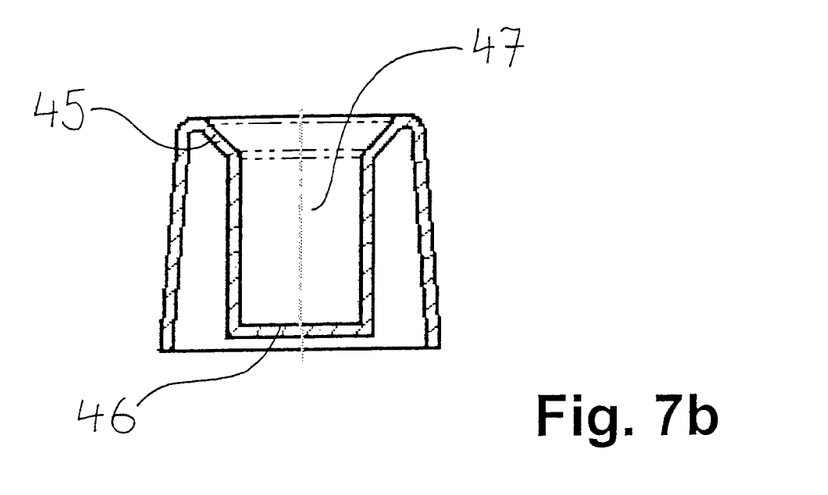
FIG. 7b is a longitudinal section of a reagent container of a beaker-like shape.

FIG. 7b shows a longitudinal section of a reagent container 47 of a beaker-like shape with an impermeable inner surface. An overflow channel 45 extends along the inner side at the upper edge of the reagent container 47. A reagent liquid, which is not shown here and into which the sample collector is introduced following the sampling of saliva, is filled into the bottom 46 of the reagent container 47. The reagent liquid is pressed into the pores of the sample collector by applying pressure to the sample collector, and excess reagent liquid is left in the overflow channel 45 of the reagent container 47. Mixing of the reagent liquid with the saliva, and dilution and subsequent filtration of the saliva are brought about in the pores of the sample collector. The saliva sample thus processed collects in the cavity 10 of the sample collector.

Figure 8:
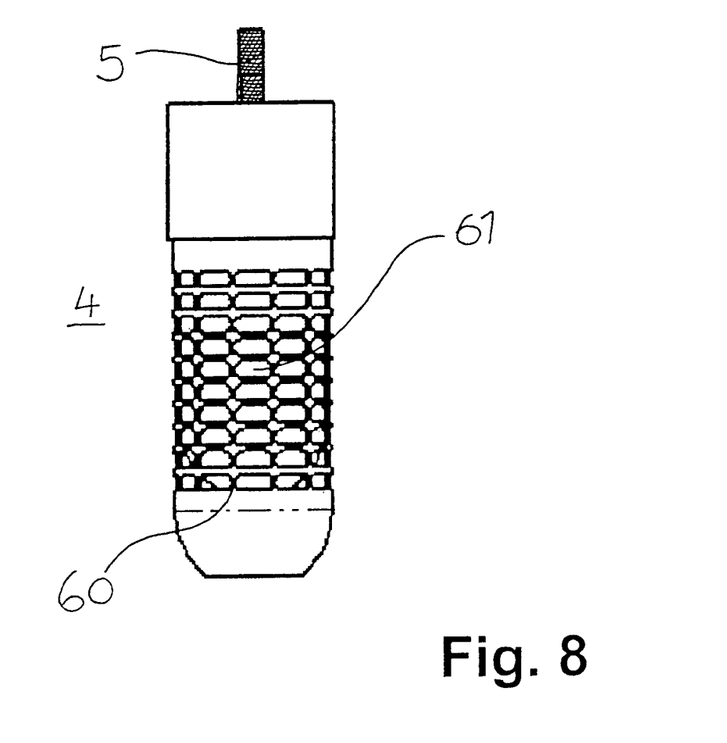
FIG. 8 is a top view of another embodiment of a mouthpiece.

FIG. 8 shows another embodiment of a mouthpiece 4 with an indicator zone 5 designed as an indicator tab. The mouthpiece 4 is not made of a homogeneous material or material composite, but it consists of an incompressible sieve body 60 in the sense of a skeleton with a porous, absorbent and sponge-like content 61.

While specific embodiments of the invention have been shown and described in detail to illustrate the application of the principles of the invention, it will be understood that the invention may be embodied otherwise without departing from such principles.

What is claimed is:

1. A system for collecting and releasing a sample liquid, the system comprising:
   a sample collector having a cylindrical shape with first and second axial ends, said sample collector includes a sampling tip arranged at said first axial end, said sampling tip being formed of a porous material that collects and holds by capillary action the sample liquid, said sample collector defining a cavity adjacent to said sampling tip;
   a pressure device connectable with said sample collector for generating an overpressure in said sampling tip, said pressure device being arranged at said first axial end of said sample collector, the overpressure generated by said pressure device delivering the sample liquid from said sampling tip to said cavity of said sample collector.

2. A system in accordance with claim 1, wherein:
   said pressure device includes a container defining a volume, said first axial end of said sample collector being insertable into said volume to generate the overpressure.

3. A system in accordance with claim 2, wherein:
   said sample collector includes a sealing lip, said sealing lip sealing said volume of said container when said first axial end is inserted into said volume, said sealing lip and said sample tip being arranged and formed to have the overpressure generated when said sample collector is inserted into said volume, force the sample liquid from the sampling tip to said cavity of said sample collector.

4. A system in accordance with claim 1, further comprising:
   said pressure device includes a beaker-shaped reagent container with an impermeable inner surface, said beaker-shaped reagent container defines a volume which is open at one end, said sampling tip being insertable into said volume, wherein said sampling tip and said beaker-shaped reagent container fully enclose the volume when said sampling tip is inserted into said reagent container.

5. A system in accordance with claim 4, wherein:
   said sample collector includes a sealing lip, said sealing lip sealing said volume of said container when said first axial end is inserted into said volume so that said overpressure can be generated in the pores of the sampling tip.

6. A system in accordance with claim 4, wherein:
   said reagent container has a size and shape to press reagent liquid in said volume into pores of said sample collector when said sample collector is inserted into said reagent container.

7. A system in accordance with claim 6, wherein:

said reagent container includes an overflow channel along an inner side open end for receiving excess reagent when said sample collector is inserted into said reagent container, said size and shape of said reagent container presses the reagent liquid into said cavity of said sample collector when said sample collector is inserted into said chamber.

8. A system in accordance with claim 1, wherein:

said material of said sampling tip is treated with an additional material to further absorb the sample liquid.

9. A system in accordance with claim 1, wherein:

said sampling tip has a moisture indicator which indicates a collection of the predetermined amount of sample liquid in said sampling tip.

10. A system in accordance with claim 9, wherein:

said moisture indicator is one of an indicator dye and a material that expands in the presence of moisture.

11. A system in accordance with claim 9, wherein:

said sampling tip has an outer portion extending out of said first axial end of said sample collector, said sampling tip having an inner portion arranged inside said sample collector;

said moisture indicator being arranged at said inner portion of said sampling tip.

12. A system in accordance with claim 1, wherein:

said material of said sampling tip is dimensionally stable during collection of the sample liquid, said material of said sampling tip collecting the predetermined amount of the sample liquid by capillary action.

13. A system in accordance with claim 1, wherein:

said cavity is arranged inside said sample collector.

14. A system in accordance with claim 2, wherein:

said pressure means is displaceable relative to said sample collector, and pushing together of said pressure means and said sample collector generates the overpressure in said sampling tip to release the sample liquid from the sampling tip into said cavity, said pressure means is provided to bring about penetration of a reagent liquid from said container into said sampling tip during the pushing together of said pressure means and said sample collector.

15. A system in accordance with claim 2, further comprising:

a reagent liquid arranged in said container.

16. A system in accordance with claim 15, wherein:

said reagent container has a size and shape to press the reagent liquid in said container into pores of said sample collector when said sample collector is inserted into said container.

17. A system in accordance with claim 16, wherein:

said reagent container includes an overflow channel along an inner side at said open end for receiving excess reagent when said sample collector is inserted into said chamber.

said size and shape of said reagent container presses the reagent liquid into a cavity of said sample collector when said sample collector is inserted into said chamber.

* * * * *